United States Patent
Eriksson et al.

(10) Patent No.: US 6,768,783 B2
(45) Date of Patent: Jul. 27, 2004

(54) METHOD AND ARRANGEMENT RELATING TO AN X-RAY IMAGING APPARATUS

(75) Inventors: Rolf Eriksson, Orebro (SE); Mats Danielsson, Taby (SE)

(73) Assignee: Mamea Imaging AB, Stockholm (SE)

( * ) Notice: Subject to any disclaimer, the term of this patent is extended or adjusted under 35 U.S.C. 154(b) by 0 days.

(21) Appl. No.: 10/201,829

(22) Filed: Jul. 23, 2002

(65) Prior Publication Data

US 2003/0161439 A1 Aug. 28, 2003

(Under 37 CFR 1.47)

Related U.S. Application Data

(63) Continuation of application No. PCT/SE01/00138, filed on Jan. 24, 2001.
(60) Provisional application No. 60/178,839, filed on Jan. 24, 2000.

(51) Int. Cl.[7] .................................................. A61B 6/04
(52) U.S. Cl. ........................................ 378/37; 378/208
(58) Field of Search ........................... 378/37, 62, 145, 378/155, 195, 196, 197, 208

(56) References Cited

U.S. PATENT DOCUMENTS

| | | | |
|---|---|---|---|
| 4,907,251 A | | 3/1990 | Mork et al. |
| 4,998,270 A | * | 3/1991 | Scheid et al. ............... 378/155 |
| 5,099,503 A | * | 3/1992 | Strommer ..................... 378/37 |
| 5,335,257 A | * | 8/1994 | Stunberg ...................... 378/37 |
| 5,349,625 A | | 9/1994 | Born et al. |
| 5,627,869 A | * | 5/1997 | Andrew et al. ............... 378/37 |

\* cited by examiner

*Primary Examiner*—David V. Bruce
*Assistant Examiner*—Courtney Thomas
(74) *Attorney, Agent, or Firm*—Oppedahl & Larson LLP

(57) ABSTRACT

The present invention relates to an arrangement for adjusting a number of settings in an x-ray imaging apparatus (10) for recurrent mammography examinations, said apparatus comprising at least one x-ray source (11), a collimator arrangement (12) and compression pedals (13a, 13b) for positioning and compressing the breast (14) of a patient to be examined. The arrangement comprises: control units (16–19) for adjusting said number of settings of said x-ray imaging apparatus based on an identity of said person to be examined and data stored in a database (21), said data including a set of setting-data from at least one recent x-ray examination of said patient, a main control unit (15) communicating with a control unit (16) for adjusting characteristics of x-ray radiations from said x-ray source (11), a control unit (17) for adjusting the position of said x-ray source (11) and an identity input device (20). The arrangement further comprises a device (19) for adjusting collimator slots widths based on information retrieved from said database and/or a position of said pedals.

18 Claims, 1 Drawing Sheet

METHOD AND ARRANGEMENT RELATING TO AN X-RAY IMAGING APPARATUS

This application is a continuation of International Application Serial No. PCT/SE10/00138 designating the United States, filed on Jan. 24, 2001 and which claims the benefit of U.S. Provisional Application No. 60/178,839, filed Jan. 24, 2000.

TECHNICAL FIELD OF THE INVENTION

The present invention relates to a method and an arrangement for adjusting a number of settings in an x-ray imaging apparatus for recurrent mammography examinations, said apparatus comprising at least one x-ray source, a collimator arrangement and compression pedals for positioning and compressing the breast of a patient to be examined. The arrangement comprises: control units for adjusting said number of settings of said x-ray imaging apparatus based on an identity of said person to be examined and data stored in a database, said data including a set of setting-data from at least one recent x-ray examination of said patient, a main control unit communicating with a control unit for adjusting characteristics of x-ray radiations from said x-ray source, a control unit for adjusting the position of said x-ray source, and an identity input device.

BACKGROUND OF THE INVENTION

The adjustment of an x-ray imaging apparatus and specially a mammogrphic imaging apparatus is normally a time consuming and labourious work, specially for a nurse or the operator responsible of the per-adjustment. For each person to be examined, usually several settings must be modified. The settings include the physical features of the apparatus such as the height of the x-ray source and the breast compression arrangement, respectively, with respect to the physical appearance of the patient, and the x-ray intensity and spectrum, e.g. through adjustment of the amount of power to the radiation source, the current between the anode and cathode of the x-ray tube and filtration of the x-rays.

U.S. Pat. No. 5,349,625 describes an x-ray diagnostics installation for peripheral angiography examinations includes a control unit having an arithmetic unit that, on the basis of subject-related data supplied thereto, effects a pre-setting of the electrical parameters of the installation required for every exposure, plus the step length and the number of steps of the relative adjustment of the exposure unit and the patient support relative to one another, as well as the required diaphragm setting. By virtue of the pre-setting, stress on the patient is reduced, and since the overall time per examination is also reduced, patient throughput can be increased.

In U.S. Pat. No. 4,907,251, a patient positioning device in a medical panorama X-ray photographing apparatus in which after data of the relative position of the subject to the X-ray photographing apparatus supplied from a sensor is compared with data of the relative position of a tomographic zone to the X-ray photographing apparatus thus to produce comparison data which is in turn transmitted to a drive circuit, a tomograph forming assembly and/or the subject is moved from coinciding with each other. The device further includes a comparing arithmetic circuit in which the detected position data of the subject and position data of the tomographic zone are arithmetically compared in order to improve operatability and positioning accuracy. The device furthermore includes a sensor, which is adjustable for angular and vertical setting with the use of sensing position changing means in order to improve adaptability to individualities of the subject.

These documents, however, do not consider the specific problems related to mammography, i.e. placing the breast of the patient in a correct position and compressing it to obtain an even tissue compression for obtaining good resolution.

SUMMARY OF THE INVENTION

What is needed is an arrangement that allows an x-ray imaging apparatus, specially an apparatus for mammographic examination, to automatically assume settings specific for a certain person to be examined.

Advantages with the arrangement according to the present invention are that the burden on the operator and the patient reduces and the number of persons which can be examined and the examination flow increase as the pre-adjustment time reduces.

For this reason the initially mentioned arrangement further comprises a device for adjusting collimator slots widths based on information retrieved from said database and/or a position of said pedals. Moreover, the arrangement comprises means to detect the positions of said pedals, a compression sensor for sensing a pressure exerted by said pedals onto said breast and adjusting said pressure and position sensors for positioning said x-ray source. The identity input device is any one of a card reading device, a finger print sensor, a pin-code input device or a keyboard The invention also relates to a method in initially mentioned arrangement, which is characterised by the steps of: claiming an identity of said patient, upon receiving said identity retrieving a set of setting data from at least one last x-ray examination of said person and/or a position of said pedals, and adjusting collimator slots' widths based on said information. According to the method under a first time examination of said person, a substantially manual adjustment is carried out and results of said substantially manual adjustment are registered for later examinations.

BRIEF DESCRIPTION OF THE DRAWING

In the following, the invention will be further described in a non limiting way with reference to the accompanying drawing, in which.

DETAILED DESCRIPTION OF ONE EMBODIMENT

Figure 1:
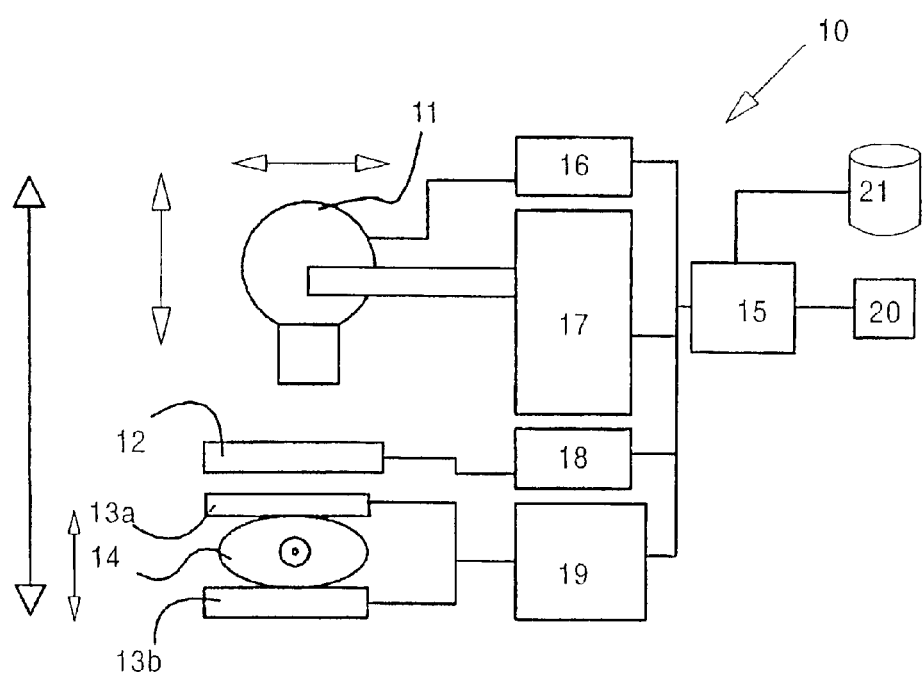
FIG. 1 is a schematic diagram illustrating an x-ray imaging according to the present invention.

FIG. 1 is a schematic diagram of a system employing an arrangement according to the invention, specially for mammography examining apparatus.

The essential parts of the system 10 comprise a radiation source 11, collimator means 12 and a pedal pares, including first and second compression pedals 13a and 13b, respectively. The female breast 14 is positioned between the compression pedals 13a and 13b. The upper compression pedal 13a is at least partly transparent to the x-ray radiation while lower pedal 13b can contain a film or a detector assembly (not shown).

The arrangement according to the invention mainly comprises a main control unit 15 and connected to it sub-control units 16–19. The sub-control unit 16 is an x-ray source controller and for instance controls the x-ray intensity by controlling power level to the tube and the current between the cathode and anode of the x-ray tube. The sub-controller 17 is a step motor or the like for relocating the x-ray source 11 in horizontal and/or vertical directions with respect to the breast's 14 position. The sub-controller denoted 18 adjusts the collimator 12 features, e.g. the width of the collimator slots. The sub-controller 19 is a device, such as a step motor which displaces the pedals 13a, 13b relative each other and controls the pressure exerted onto the breast 14. It is also possible to move the entire apparatus including the x-ray source and the pedals 13a/13b vertically to adopt it to the patient's height.

One important feature is that the collimator slit's width can be adjusted with regard to the patient data and/or the compressed breast thickness (distance between the pedals) to adjust the radiation dose. Hence, there is no need to adjust the slits' widths (in multi slits collimators) under the examining.

The main control unit 15 also includes or communicates with an input device 20 and a data storage unit (database) 21. The function of the control unit includes controlling the sub-control units based on the input from the input device and the storage unit. The input device may be any of a card reading device, a biometric sensor, a PIN code input device, keyboard etc., well known for a skilled person. The storage unit may be any of a memory unit, hard disk, CD-ROM etc., used for storing data. Clearly, the storage unit may be implemented as a part of a Local Area Network (LAN), Wide Area Network (WAN), Internet, Intranet etc., with which the main control unit communicates. The main control unit has a computer unit structure of known type and mainly comprises a processing unit (not shown), memory and interfaces for communication with the other units or devices.

The invention is most suitable for recurrent x-ray examinations, e.g. mammographic examinations and specially for mass screening situations, as the settings of the system are depending on the patient's physical appearance, such as length, breast thickness etc. The invention may also be used for bone densitometry examination.

Following Non Limiting Example Simplifies the Underrating of the Invention:

If it is the first time examining a person, the height of the pedals 13a, 13b, and the x-ray source is adjusted in a known way with respect to the height of the patient and the breast of the person is placed in between the compression pedals 13a, 13b exercising an amount of pressure on the breast. The height of the pedals and the source are registered automatically by means of sensors (or manually) and stored in a database 21 with relation to the patient identity. Depending on the breast or tissue thickness, the intensity, and exposure area and time of the x-ray beam is adjusted by adjusting the power and the current to the tube and possibly by adjusting the collimator 12. All settings are stored in the above-mentioned database for later use. Sensors are provided for reading the setting values, however, a manual reading and data entering may occur.

If the examination concerns a person having been examined before and her relevant data is stored in the database, the system is activated by entering her identity through the input device 20, which can be an identity number, a social security number, a finger print or any other unique identifying code. Based on the identity of the person to be examined, and preferably after an identity check, the main control unit retrieves the height, pedal pressure, x-ray intensity, focussing and exposure time and other relevant data from the database 21. The main control unit controls the sub-control units 16–19 with respect to the data retrieved from the database. When the patient is placed on the x-raying, the step motor 17 positions the x-ray source 11 in a correct height, the pedals 13a and 13b are brought into correct height and the operator helps placing the breast of the patient between the pedals, which then brought together by the step motor 19 to compress the breast into a substantially flat body for best contrast. Then the x-ray source is controlled based on the breast thickness to radiate with correct power. If there is a need for readjustment of the settings, the new settings are stored.

The system may be expanded by storing the x-ray images in digital form, which for example can be used to inspect tumour changes.

The invention is not limited the shown embodiments but can be varied in a number of ways without departing from the scope of the appended claims and the arrangement and the method can be implemented in various ways depending on application, functional units, needs and requirements etc.

What is claimed is:

1. An arrangement for adjusting a number of settings in an X-ray imaging apparatus for recurrent mammography examinations, said apparatus including at least one X-ray source, a collimator arrangement and compression pedals for positioning and compressing the breast of a patient to be examined, said arrangement comprising control units for adjusting said number of settings of said X-ray imaging apparatus based on an identity of said patient to be examined and data stored in a database, said data including a set of setting data from at least one recent X-ray examination of said patient, a main control unit communicating with a control unit for adjusting characteristics of X-ray radiations from said X-ray source, a control unit for adjusting the position of said X-ray source, and an identity input device, characterized in that said arrangement further comprises a device for adjusting collimator slots' widths based on information retrieved from said database, or a position of said pedals, or both.

2. The arrangement according to claim 1, comprising means to detect the positions of said pedals.

3. The arrangement according to claim 1, comprising a compression sensor for sensing a pressure exerted by said pedals onto said breast and adjusting said pressure.

4. The arrangement according to claim 2, comprising a compression sensor for sensing a pressure exerted by said pedals onto said breast and adjusting said pressure.

5. The arrangement according to claim 1, characterized in that said identity input device is any one of a card reading device, a finger print sensor, a PIN-code input device or a keyboard.

6. The arrangement according to claim 2, characterized in that said identity input device is any one of a card reading device, a finger print sensor, a PIN-code input device or a keyboard.

7. The arrangement according to claim 3, characterized in that said identity input device is any one of a card reading device, a finger print sensor, a PIN-code input device or a keyboard.

8. The arrangement according to claim 4, characterized in that said identity input device is any one of a card reading device, a finger print sensor, a PIN-code input device or a keyboard.

9. The arrangement according to claim 1, characterized in that it comprises position sensors for positioning said X-ray source.

10. The arrangement according to claim 2, characterized in that it comprises position sensors for positioning said X-ray source.

11. The arrangement according to claim 3, characterized in that it comprises position sensors for positioning said X-ray source.

12. The arrangement according to claim 4, characterized in that it comprises position sensors for positioning said X-ray source.

13. The arrangement according to claim 5, characterized in that it comprises position sensors for positioning said X-ray source.

14. The arrangement according to claim 6, characterized in that it comprises position sensors for positioning said X-ray source.

15. The arrangement according to claim 7, characterized in that it comprises position sensors for positioning said X-ray source.

16. The arrangement according to claim 8, characterized in that it comprises position sensors for positioning said X-ray source.

17. A method for use with an X-ray imaging apparatus for recurrent mammography examinations, said apparatus including at least one X-ray source, a collimator arrangement and compression pedals for positioning and compressing the breast of a patient to be examined, said arrangement comprising:

control units for adjusting said number of settings of said X-ray imaging apparatus based on an identity of said patient to be examined and data stored in a database, said data including a set of setting-data from at least one recent X-ray examination of said patient, a main control unit communicating with a control unit for adjusting characteristics of X-ray radiations from said X-ray source, a control unit for adjusting the position of said X-ray source, and an identity input device, the method comprising the steps of obtaining an identity of said patient, upon receiving said identity retrieving a set of setting data from at least one previous X-ray examination of said patient or a position of said pedals or both, and adjusting collimator slots' widths based on said retrieved set of setting data.

18. The method according to claim 17, characterized in that upon a first-time examination of said patient, a substantially manual adjustment is carried out and results of said substantially manual adjustment are registered for later examinations.

* * * * *